United States Patent
O'Gara et al.

(10) Patent No.: US 8,445,012 B2
(45) Date of Patent: May 21, 2013

(54) COMPOSITIONS AND METHODS FOR DELIVERY OF EMBOLICS

(75) Inventors: John O'Gara, Ashland, MA (US); Sonali Puri, Ashland, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 13/350,123

(22) Filed: Jan. 13, 2012

(65) Prior Publication Data

US 2012/0114749 A1    May 10, 2012

Related U.S. Application Data

(63) Continuation of application No. 12/381,264, filed on Mar. 10, 2009, now Pat. No. 8,114,436.

(60) Provisional application No. 61/070,682, filed on Mar. 25, 2008.

(51) Int. Cl.
| | | |
|---|---|---|
| *A61K 9/66* | (2006.01) | |
| *A61K 9/20* | (2006.01) | |
| *A61K 9/16* | (2006.01) | |
| *A61K 9/50* | (2006.01) | |

(52) U.S. Cl.
USPC .......... 424/455; 424/464; 424/490; 424/493; 424/497

(58) Field of Classification Search
None
See application file for complete search history.

(56) References Cited

U.S. PATENT DOCUMENTS

| 4,136,145 A | 1/1979 | Fuchs et al. |
|---|---|---|
| RE33,375 E | 10/1990 | Luck et al. |
| 4,994,069 A | 2/1991 | Ritchart et al. |
| 5,700,476 A | 12/1997 | Rosenthal et al. |
| 5,912,017 A | 6/1999 | Mathiowitz et al. |
| 6,676,971 B2 | 1/2004 | Goupil et al. |
| 6,680,046 B1 | 1/2004 | Boschetti |
| 7,008,642 B1 | 3/2006 | Roorda et al. |
| 7,311,861 B2 | 12/2007 | Lanphere et al. |
| 2003/0032935 A1 | 2/2003 | Damiano et al. |
| 2004/0076582 A1 | 4/2004 | Dimatteo et al. |
| 2005/0131458 A1 | 6/2005 | Batich et al. |
| 2005/0142202 A1 | 6/2005 | Roorda et al. |
| 2005/0181050 A1 | 8/2005 | Hirsh et al. |

FOREIGN PATENT DOCUMENTS

WO    03094930 A1    11/2003

OTHER PUBLICATIONS

Coldwell et al. (Radiographics 1994, 14:623-643).
Pal et al. (AAPS PharmSciTech published Mar. 16, 2007; 8(1) pp. E1-E5).
Ball, et al., "In Vitro Stability of Tris-Acryl Gelatin Microspheres in a Multipharmaceutical Chemoembolization Solution," J Vasc Intervent Radiol 14:83-88 (1998).
Beaujeux, et al., "Trisacryl Gelatin Microspheres for Therapeutic Embolization, II: Preliminary Clinical Evaluation in Tumors and Arteriovenous Malformations," Am J Neuroradiol 17:541-548 (1996).
Brown, et al., "Particle Embolization for Hepatocellular Carcinoma," J Vasc Intervent Radiol 9:822-828 (1998).
Misirli, et al., "Preparation and Characterization of Mitomycin-C Loaded Chitosan-Coated Alginate Microspheres for Chemoembolization," J Microencapsul 22:167-178 (2005).
Rand, et al., "Arterial Embolization of Unresectable Hepatocellular Carcinoma With Use of Microspheres, Lipiodol, and Cyanoacrylate," Cardiovasc Intervent Radiol 28:313-318 (2005).

*Primary Examiner* — Ernst Arnold
(74) *Attorney, Agent, or Firm* — Mayer & Williams PC; David B. Bonham

(57) ABSTRACT

Described herein are compositions comprising one or more embolics attached to an inert, dissolvable matrix as well as kits comprising these novel embolic formulations. Also described are methods of making and using these embolic formulations.

22 Claims, 1 Drawing Sheet

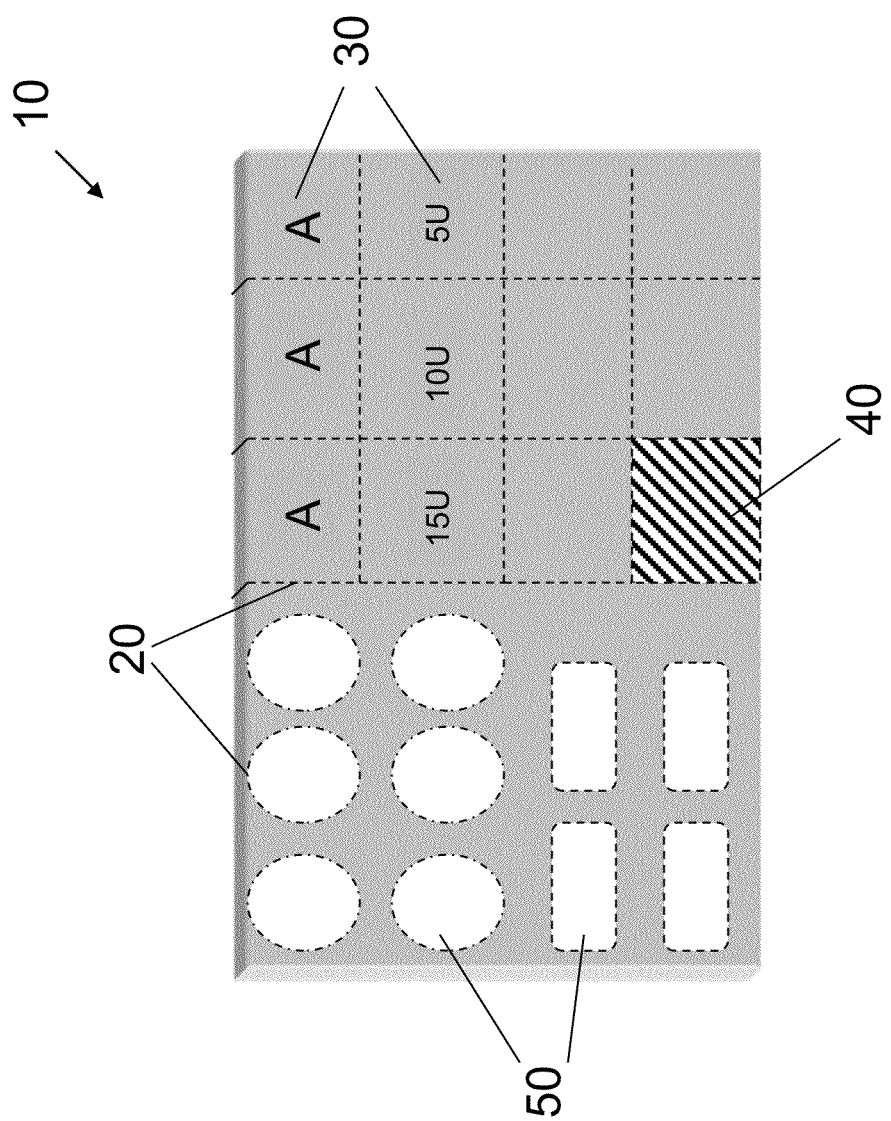

COMPOSITIONS AND METHODS FOR DELIVERY OF EMBOLICS

CROSS-REFERENCE TO RELATED APPLICATIONS

The present application is a continuation of U.S. patent application Ser. No. 12/381,264, filed Mar. 10, 2009, now U.S. Pat. No. 8,114,436, the disclosure of which is hereby incorporated by reference in its entirety, and which claims the benefit of U.S. Provisional Application No. 61/070,682, filed Mar. 25, 2008, the disclosure of which is hereby incorporated by reference in its entirety.

TECHNICAL FIELD

This disclosure relates to embolic compositions, including novel packaging formats useful in delivering customized amounts of embolics.

BACKGROUND

Embolic agents are useful for a variety of bioapplications, such as occluding blood vessels, occluding aneurysms, occluding other body lumens such as fallopian tubes, filling aneurysm sacs, as arterial sealants, and as puncture sealants.

Embolization of blood vessels is performed for a number of reasons, e.g. to reduce blood flow to and encourage atrophy of tumors, such as in the liver, to reduce blood flow and induce atrophy of uterine fibroids, for treatment of vascular malformations, such as arteriovenous malformations (AVMs) and arteriovenous fistulas (AVFs), to seal endoleaks into aneurysm sacs, to stop uncontrolled bleeding, or to slow bleeding prior to surgery. An aneurysm (a dilation of a blood vessel) poses a risk to health from the potential for rupture, clotting, or dissecting. Rupture of an aneurysm in the brain causes stroke, and rupture of an aneurysm in the abdomen causes shock.

Gynecologic embolotherapy may be conducted for a variety of purposes including the treatment of uterine fibroids, the treatment of postpartum and post caesarean bleeding, the treatment of post surgical vaginal bleeding, the prevention and/or treatment of hemorrhage from ectopic pregnancy, prophylactically prior to myomectomy and in obstetrical patients at high risk for bleeding, such as those patients with placenta previa, placenta accreta, uterine fibroids, and twin fetal death.

Embolics have also been used to treat cancer. For example, embolics can be used to occlude the vasculature feeding a solid tumor. As an adjunct to embolization, drug-loaded embolics, such as drug-loaded microspheres, have been used for in situ delivery of chemotherapeutic agents and/or therapeutic agents designed to treat inflamed or diseased tissue. In addition, clinicians have administered chemotherapeutic agents in combination with embolic PVA particles. This type of regional therapy may localize treatment at the site of the tumor, and therefore the therapeutic dose may be smaller than the effective systemic dose, reducing potential side effects and damage to healthy tissue.

Liquid embolics as well as polymer-based particles and embolic microspheres currently used for indications described above are known. See, e.g., U.S. Pat. Nos. 7,311,861 and 6,676,971 and references cited therein, incorporated by reference in their entireties herein. These embolics are usually introduced to the site of desired embolization via microcatheters.

However, embolics are currently sold in prepackaged form, for example as a vial or syringe containing a set quantity of embolic and/or drug. See, e.g., Onyx® Liquid Embolic System, sold by the Endovascular Company. As a result, the health care professional administering the embolic cannot use an amount of embolic and optional drug other than what is supplied in the container. Moreover, for embolics packaged with additional therapeutic compounds, the physician cannot alter the ratio of embolic to drug for individual patients. Changing the amount of embolic and/or the ratio of therapeutic agent to embolic requires the physician to spend extra time carefully removing the embolic from its packaging, weighing of measuring the desired amount of embolic, mixing the desired amount of embolic with a set amount of the therapeutic drug and then charging the drug-loaded embolic back into the delivery device.

Thus, there remains need for embolic formulations that allow for the health care professional to readily deliver any selected amount of embolic and/or therapeutic agent.

SUMMARY

Described herein are compositions and methods for delivering customized amounts (dosages) of embolics to a patient. The compositions and methods described herein allow for individualized single and combination therapies.

In certain aspects, described herein is a composition comprising a measured amount of one or more embolics attached to (e.g., absorbed, adsorbed and/or encapsulated) a solid, inert, dissolvable matrix. In certain embodiments, at least one embolic comprises a liquid embolic. In other embodiments, at least one embolic comprises a particulate embolic, for example, microspheres (e.g., drug-loaded microspheres).

In any of the compositions described herein, the matrix can comprise a tablet, capsule and/or sheet. In certain embodiments, the matrix comprises a sheet comprising outlines or perforations around a measured amount of the embolics. The matrix may comprise a carbohydrate (e.g., sugar, starch, sugar alcohol and/or honey), a clay, a cellulose, an algin, a gum, a polymer (e.g., naturally occurring polymer such as gelatin, synthetic polymer, cross-linked polymer) or combinations thereof. In any of the compositions described herein, the matrix may dissolve in water, saline, plasma and/or blood.

In another aspect, described herein is a kit comprising: one or more compositions as described herein; and written instructions for dissolving the matrix. Any of the kits described herein may further comprise one or more solutions for dissolving the matrix.

In yet another aspect, the disclosure provides a method of preparing a solution comprising a customized amount of one or more embolics, the method comprising: placing one or more compositions as described herein containing the customized amount of embolics into a solution that dissolves the matrix. In certain embodiments, the solution comprises one or more drugs (e.g., chemotherapeutic agent(s), anesthetic(s) or anti-inflammatory(ies).

In another aspect, described herein is a method of administering a customized amount of an embolic to a subject, the method comprising: preparing a customized amount of an embolic according to any of the methods described herein; and administering the solution containing the selected amount of embolic to the subject.

In yet another aspect, provided herein is a method of treating a disease or symptom susceptible to treatment with an embolic, the method comprising: administering a customized amount of an embolic to a subject in need thereof according to any of the methods described herein in an amount sufficient to ameliorate the disease or symptom. In certain embodiments, the disease or symptom is selected from the group consisting of an aneurysm, an arteriovenous malformation (AVM), an arteriovenous fistulas (AVF); an endoleak; a hemorrhagic process, slowing bleeding prior to surgery; uterine fibroids, cancer, pain, excess bleeding, and combinations thereof.

These and other embodiments will readily occur to those of skill in the art in light of the disclosure herein.

BRIEF DESCRIPTION OF THE FIGURES

FIG. 1 is an overview of an exemplary dissolvable sheet comprising one or more embolics 10 as described herein. The sheet can include perforations 20 or lines that delineate areas 50 containing particular concentrations of the embolic(s). Additional markings 30, colors or patterns 40 can be placed on the sheet to indicate different concentrations of the embolic on the same sheet.

DETAILED DESCRIPTION

Compositions comprising embolics and methods of using these embolics are described herein. In particular, novel packaging formats and packaging materials that allow physicians to easily administer customized amounts and combinations of one or more embolics with one or more therapeutics agents are provided. Methods of making and using customized amount of embolic and/or drug compositions are also described.

All publications, patents and patent applications cited herein, whether above or below, are hereby incorporated by reference in their entirety.

It must be noted that, as used in this specification and the appended claims, the singular forms "a", "an", and "the" include plural references unless the content clearly dictates otherwise.

The practice of the present invention will employ, unless otherwise indicated, conventional techniques of pharmaceuticals, embolics and embolization therapies. Such techniques are explained fully in the literature, such as, *Remington's Pharmaceutical Sciences,* 17th ed. (1989); *Handbook of Pharmaceutical Manufacturing Formulations* Volumes 1-6 by Sarfaraz K. Niazi (CRC Press, 2004); *Vascular Embolotherapy: A Comprehensive Approach Volume 1: General Principles, Chest, Abdomen, and Great Vessels* (J. Golzarian ed., Springer, 1986); *Microspheres and Regional Cancer Therapy* by Neville Willmott & John M. Daly (CRC Press, 1993); and *Tissue Adhesives in Clinical Medicine* by James Quinn, M.D. (BC Decker Inc., $2^{nd}$ ed., 2005).

Compositions Of The Invention

The present invention includes novel embolic packaging configurations and format that allow for quick and accurate measurement of custom amounts of embolic materials, alone or in combination with other embolics and/or therapeutic agents.

In particular, the present disclosure relates to embolic materials that are packaged in a dissolvable matrix (e.g., embedded in and/or otherwise attached to the matrix). Prior to delivery, the matrix is dissolved such that a precise amount of embolic and optional additional therapeutics can be administered to a subject. Thus, unlike many previously disclosed matrix-containing pharmaceutics in which the matrix (with embedded pharmaceuticals) is delivered to a patient (see, e.g., U.S. Pat. Nos. 4,136,145; 5,700,476; 7,008,642; Reissue No. 33,375; and U.S. Patent Publication No. 20050181050), the compositions and methods described herein involve dissolution of the matrix prior to delivery to the subject.

In certain aspects, a pre-set amount (by weight or volume) of an embolic (liquid or microspheres) is absorbed, adsorbed and/or encased in an inert tablet or capsule matrix using methods known in the art. The matrix is selected such that it readily dissolves in any selected biocompatible solution, including, by way of example only, a drug solution, a saline solution and/or a contrast agent solution. See, e.g., *Remington's Pharmaceutical Sciences,* 17th ed. (1989).

When the matrix dissolves, the embolic is released into the solution at known concentration. Additional tablet or capsule matrices containing the same or different concentrations of the same or different embolic can be added to the solution to prepare a solution containing a precise and desired amount of embolic(s). This system also allows the physician to add a desired amount of one or more therapeutic agents to the embolic solution, thereby customizing the amounts of drug delivered to a patient using an embolic. Since it is desirable for the therapeutic agent to be released over time from the embolization mass formed by the embolic, in such embodiments, the embolic and/or therapeutic agents may be selected for their ability to bind one another.

In other aspects, pre-measured amount (by weight or volume) of an embolic (liquid or microspheres) is absorbed, adsorbed and/or encased in a dissolvable sheet of matrix material, as depicted in FIG. 1. Outlined and/or perforations 20 can be used to define areas 50 (e.g., squares, rectangles, circles, ovals etc.) of the sheet containing specified amounts of the embolic. In addition, markings 30, patterns 40 or colors may be included to indicate embolic concentration(s). The sheet is dissolvable in any biocompatible solution as described above to prepare a metered dose of embolic, which in turn can be optimized to include a metered dose of one or more therapeutic agents.

The tablet, capsule or sheet as described herein will typically contain between about 0.1 mL and 5 mL of one or more embolization liquid, particles and/or microspheres, for example, between 0.1 and 2.5 mL, between 2.5 and 5.0 mL, or between 0.1 and 1 mL of embolic(s).

In any of the embodiments described herein, the embolic material can be lyophilized (freeze dried) prior to mixing with tablet or sheet fillers. Upon dissolution of the matrix in the solution, the embolic will rapidly swell back to a therapeutically beneficial size and shape. Methods of preparing such tablets are known in the art and include, by way of example, direct compression, compression-molding and encapsulation techniques. See, e.g., *Remington's Pharmaceutical Sciences,* 17th ed. (1989).

Any dissolvable material can be used for the matrix (e.g., tablet, capsule or sheet). Such materials are well known in the pharmaceutical field and include, but are not limited to, carbohydrates (e.g., sugars, starches, lactose, honey, sugar alcohols and tetroses); clays; celluloses; algins; gums; and/or naturally occurring or synthetic polymers such as gelatin, PLGA, including cross-linked polymers.

As noted above, the matrix is typically chosen so as to rapidly dissolve in a selected solution. Disintegration of the embolic matrix can be hastened in some instances, for example by the addition of excipients such as superdisintegrants that aid in dissolving the tablet, capsule or sheet in a fluid environment. Non-limiting examples of dissolving excipients include croscarmelose, crospovidone, low-substituted hydroxypropyl cellulose and sodium starch glycolate.

Any embolic material can be packaged as described herein, including but not limited to liquid embolics such as cyanoacrylates and/or particle embolic materials such as embolization microspheres.

In certain embodiments, the packaged embolic material comprises an embolization microsphere. Embolization microspheres are occlusive agents composed of both resorbable and nonresorbable materials, including polyvinyl alcohol, chitosan-coated alginate, degradable starch, aromatic oil gelatin, ethyl cellulose, albumin, dextran, glass, wax, silicone, polystyrene and polyacrylates. Beaujeux et al. (1996) *Am J Neuroradiol* 17:541-548; Brown et al. (1998) *J Vasc Intervent Radiol* 9:822-828; Rand et al. (2005) *Cardiovasc Intervent Radiol* 28:313-318; Ball D S et al. (2003) *J Vasc Intervent Radiol* 14:83-88; Misirli et al. (2005) *J Microencapsul* 22:167-178; U.S. Pat. No. 6,680,046. Multi-layered microspheres are also known. See, e.g., U.S. Pat. No. 5,912,017. Microspheres containing therapeutic agents have also been disclosed, for example microspheres with radioactive species (e.g., U.S. Patent Publication No. 20040076582), chemotherapeutics, or the like.

Embolic microspheres are commercially available, for example CELPHERE® microspheres (Asahi-Kasei Co. Ltd., Tokyo, Japan) as well as Embosphere® Microspheres, EmboGold™, HepaSphere™ and QuadraSphere™ (Biosphere Medical™ Inc.). Likewise, microspheres comprising therapeutic agents are also commercially available, including, for example, Paclimer®, a biodegradable polymer microsphere formulation containing 10% (w/w) paclitaxel.

As noted above, therapeutic agents that can be added to the solution containing the embolic and dissolved matrix include, but are not limited to, radioactive species, chemotherapeutics (e.g., paclitaxel, doxorubicin, daunorubicin, and epirubicin), antibiotics, anesthetic agent, anti-inflammatory and the like. In some embodiments, the embolic is pre-loaded with a drug, for example a microsphere that encapsulates the drug. In such cases, the drug added to the solution can be the same drug (to achieve a higher dosage) or a different drug (for combination therapies). In any of the compositions described herein, the embolic and/or therapeutic agent may be selected based on their capacity to bind to each other.

Methods Of The Invention

Described herein are methods of making customized embolic formulations as well as methods of using these customized formulations for treatment of any disorder which is susceptible to treatment by embolization.

In certain embodiments, the methods comprise preparing an embolic formulation by attaching (adsorbing, absorbing, encapsulating) a measured amount of one or more embolics to a dissolvable matrix. The embolics may be, for example, liquid embolics or particle embolics, including microspheres and drug-loaded microspheres. The embolic formulation is attached to the matrix using standard techniques. As noted above, any biocompatible, dissolvable matrix can be used, including a tablet, capsule and/or sheet formulation. Different concentrations and/or combinations of embolics can be attached to a single matrix. For example, color coding can be used for compositions having particular concentrations of embolic. For sheet formulations, the area containing the measured amount of embolic(s) is preferably outlined and/or perforated to delineate the area containing the known amount of embolic.

Methods of preparing a solution comprising a customized amount of an embolic for delivery to a subject are also provided. The methods involve providing one or more embolic-dissolvable matrix formulations as described herein, the embolic-dissolvable formulations having a pre-selected amount of embolic; and dissolving the matrix component of the selected formulations in a suitable, biocompatible solution, thereby preparing a solution comprising an embolic for delivery to a subject. In certain embodiments, the methods also comprise adding one or more therapeutic drugs to the biocompatible solution.

Methods of administering a customized amount of an embolic to a subject are also provided, for example by preparing a customized amount of an embolic as described herein and administering the solution containing the selected amount of embolic. Thus, the methods involve providing one or more embolic-dissolvable matrix formulations as described herein, the embolic-dissolvable formulations having a pre-selected amount of embolic; dissolving the matrix component of the selected formulations in a suitable, biocompatible solution; and administering the embolic solution to the subject. In certain embodiments, the methods also comprise adding one or more therapeutic drugs to the sterile, biocompatible solution prior to administering the solution to the patient. In addition, the customized embolics can be administered in combination with other pharmaceutical agents, as described herein, and can be combined with a physiologically acceptable carrier thereof. In any of the methods described herein, the dissolved matrix material can be removed from the embolic solution prior to administration, for example by filtration or the like.

Methods of treating a patient in need thereof with a customized embolic are also provided. The methods involve administering one or more customized embolics as described herein as to a patient in need thereof as described herein. In certain embodiments, the customized embolics are used to treat any disease or symptom by reducing blood flow. Non-limiting examples of conditions and symptoms susceptible to treatment by embolization include treatment of vascular malformations such as aneurysms, arteriovenous malformations (AVMs), arteriovenous fistulas (AVFs); sealing of endoleaks; treatment of hemorrhagic processes; slowing bleeding prior to surgery; treatment of uterine fibroids and associated symptoms (bleeding, pain, disfigurement) via uterine artery embolization (UAE); treatment of puncture wounds via sealing; treatment of tumors by reducing blood flow to the tumor; etc. In certain embodiments, the dissolved embolic formulation further comprises one or more therapeutic agents. For example, for the treatment of tumors, one or more chemotherapeutics may be added to the embolic formulation prior to administration and/or the embolic formulations may include drug (chemotherapy) loaded embolic microspheres. Furthermore, the methods of the invention may be practiced in combination with other therapies which make up the standard of care for the selected disorder or symptom, such as surgery, administration of drug agents (medical therapies) and the like. As noted above, the dissolved matrix material may optionally be removed from the solution prior to administration.

The compositions and methods described herein allow for varied treatment based on individual need and other factors evident to one skilled in the art. Factors to be considered include nature of the site of embolization, use of additional drugs, and nature of the embolic(s). Such factors are known in the art and it is well within the skill of those in the art to make such determinations without undue experimentation.

The embolics used in the methods described herein can be delivered to the target site by any suitable means. Typically, the embolics are delivered by direct injection into the vasculature using a catheter or microcatheter operably linked to a syringe with the embolic formulation. Conventional catheter insertion and navigational techniques involving guidewires or flow-directed devices may be used to access the site with a catheter. The embolic-containing solution will be such as to be capable of being advanced entirely through the catheter and placed at the target site. For use in peripheral or neural surgeries, the delivery mechanism will normally be about 100-200 cm in length, more normally 130-180 cm in length.

The diameter of the delivery mechanism is usually in the range of 0.25 to about 0.90 mm. For instance, in treatment of an aneurysm, the aneurysm itself may be filled with the embolics to cause formation of emboli.

A selected site is reached through the vascular system using a collection of specifically chosen catheters and/or guide wires. It is clear that should the site be in a remote site, e.g., in the brain, methods of reaching this site are somewhat limited. One widely accepted procedure is found in U.S. Pat. No. 4,994,069 to Ritchart, et al. Once the selected site has been reached, the embolic and optional therapeutic agents are extruded by the operator at the selected site.

As is well known in the art, solutions or suspensions used for the routes of administration described herein can include any one or more of the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

As is well known in the art, pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. Prolonged absorption of the injectable compositions can be brought about by including in the composition an agent which delays absorption, for example, aluminum monostearate and gelatin.

As is well known in the art, sterile injectable solutions can be prepared by incorporating the active compound(s) in the required amount in an appropriate solvent with one or a combination of ingredients enumerated above, as required, followed by filtered sterilization. In the case of sterile powders for the preparation of sterile injectable solutions, vacuum drying and freeze-drying yield a powder of the active ingredient plus any additional desired ingredient from a previously sterile-filtered solution thereof.

Furthermore, although intravenous administration is typical of the methods described herein, additional route(s) of administration useful in particular applications will also apparent to one of skill in the art. Routes of administration include but are not limited to topical, dermal, transdermal, transmucosal, epidermal, parenteral, gastrointestinal, and naso-pharyngeal and pulmonary, including transbronchial and transalveolar.

The above-mentioned compositions and methods of administration are meant to describe but not limit the methods of administering the formulations of the invention. The methods of producing the various compositions and devices are within the ability of one skilled in the art and are not described in detail here.

Kits

The invention also provides kits. In certain embodiments, the kits of the invention generally comprise one or more containers comprising an embolic-matrix composition as described herein. The kits may further comprise one or more solutions for dissolving the matrix component; one or more therapeutic agents; and/or a suitable set of instructions, generally written instructions, relating to the use of the embolic-matrix compositions for administration of customized amounts of embolic and therapeutic agents.

The kits may comprise the embolic-matrix composition packaged in any convenient, appropriate packaging. For example, if the embolic-matrix composition inhibitor is a dry formulation (e.g., freeze dried), a vial with a resilient stopper is normally used, so that the matrix may be easily dissolved by injecting fluid through the resilient stopper. Tablets, capsules and/or sheets may be provided in sterile wrapped containers. Typically, the kits will comprise embolic-matrix compositions having a variety of embolic concentrations so that the physician can readily dissolve the appropriate matrices to arrive at the desired final amount of embolic. In addition, kits may contain more than one embolic (in multiple concentrations), so that the physician can mix and match embolic properties (e.g., microspheres of different size or sphericity; ability of the embolic to bind to different drugs) to optimize treatment for a particular patient or patient group. Also contemplated are packages for use in combination with a specific delivery device, such as a syringe or a microcatheter.

The instructions relating to the use of the embolic-matrix compositions generally include information as to dosage, dosing schedule, and administration for the intended method of use. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

Modifications of the procedures and assemblies described above, and the methods of using them in keeping with this disclosure will be apparent to those having skill in this mechanical and surgical art. These variations are intended to be within the scope of the claims that follow.

What is claimed is:

1. A method of administering a customized amount of embolization particles to a subject need thereof, the method comprising:
preparing a solution comprising a customized amount of said embolization particles by combining the following: (a) one or more compositions that comprise a measured amount of said embolization particles attached to a solid, inert, dissolvable matrix and (b) a biocompatible solution that dissolves the matrix and releases embolization particles; and
administering the solution containing the customized amount of embolization particles to the subject.

2. A method of treating a disease or symptom susceptible to treatment with an embolic, the method comprising:
administering a customized amount of embolization particles to said subject in need thereof according to claim 1 in an amount sufficient to ameliorate the disease or symptom.

3. The method of claim 2, wherein the disease or symptom is selected from the group consisting of an aneurysm, an arteriovenous malformation (AVM), an arteriovenous fistulas (AVF); an endoleak; a hemorrhagic process, slowing bleeding prior to surgery; uterine fibroids, cancer, pain, excess bleeding, and combinations thereof.

4. The method of claim 2, wherein the method is selected from the group consisting of occlusion of blood vessels, occlusion of fallopian tubes, sealing of arteries, sealing of punctures, treatment of tumors, treatment of uterine fibroids, treatment of vascular malformations, treatment of aneurysms, treatment of postpartum bleeding, treatment of post-caesarean bleeding, treatment of post-surgical vaginal bleeding, treatment of hemorrhage from ectopic pregnancy, and treatment of cancer.

5. The method of claim 1 wherein the embolization particles are adsorbed or absorbed to the matrix.

6. The method of claim 1, wherein the embolization particles are encapsulated by the matrix.

7. The method of claim 1, wherein the embolization particles comprise microspheres.

8. The method of claim 1, wherein the embolization particles are drug-loaded.

9. The method of claim 1, wherein the matrix is selected from the group consisting of a tablet, a capsule, a sheet and combinations thereof.

10. The method of claim 1, wherein the matrix comprises a sheet and the sheet comprises outlines or perforations around a measured amount of the embolization particles.

11. The method of claim 1, wherein the matrix comprises a carbohydrate, a clay, a cellulose, an algin, a gum, a polymer or combinations thereof.

12. The method of claim 1, wherein the one or more compositions are taken from a composition that comprises defined areas of differing concentration of the embolization particles.

13. The method of claim 12 wherein the embolization particles are adsorbed or absorbed to the matrix.

14. The method of claim 12, wherein the embolization particles are encapsulated by the matrix.

15. The method of claim 12, wherein the embolization particles comprise microspheres.

16. The method of claim 12, wherein the embolization particles are drug-loaded.

17. The method of claim 12, wherein the matrix is selected from the group consisting of a tablet, a capsule, a sheet and combinations thereof.

18. The method of claim 12, wherein the matrix comprises a sheet and the sheet comprises outlines or perforations around a measured amount of the embolization particles.

19. The method of claim 12, wherein the matrix comprises a carbohydrate, a clay, a cellulose, an algin, a gum, a polymer or combinations thereof.

20. A method of treating a disease or symptom susceptible to treatment with an embolic, the method comprising:
administering a customized amount of embolization particles to said subject in need thereof according to claim 12 in an amount sufficient to ameliorate the disease or symptom.

21. The method of claim 20, wherein the disease or symptom is selected from the group consisting of an aneurysm, an arteriovenous malformation (AVM), an arteriovenous fistulas (AVF); an endoleak; a hemorrhagic process, slowing bleeding prior to surgery; uterine fibroids, cancer, pain, excess bleeding, and combinations thereof.

22. The method of claim 20, wherein the method is selected from the group consisting of occlusion of blood vessels, occlusion of fallopian tubes, sealing of arteries, sealing of punctures, treatment of tumors, treatment of uterine fibroids, treatment of vascular malformations, treatment of aneurysms, treatment of postpartum bleeding, treatment of post-caesarean bleeding, treatment of post-surgical vaginal bleeding, treatment of hemorrhage from ectopic pregnancy, and treatment of cancer.

* * * * *